United States Patent
Dykstra et al.

[11] Patent Number: 6,059,112
[45] Date of Patent: May 9, 2000

[54] PEEL PACKAGE

[75] Inventors: Scott M. Dykstra, Jenison; Mark S. Lastovich, Rockford; Geoffrey A. Pavey, Kentwood, all of Mich.

[73] Assignee: Oliver Products Company, Grand Rapids, Mich.

[21] Appl. No.: 09/352,382

[22] Filed: Jul. 13, 1999

Related U.S. Application Data

[63] Continuation-in-part of application No. 09/179,811, Oct. 27, 1998, Pat. No. 5,947,288.

[51] Int. Cl.[7] .................................................. B65D 27/32
[52] U.S. Cl. ...................... 206/438; 206/467; 206/484.2; 383/111
[58] Field of Search .................................... 383/109, 111, 383/113; 206/438, 439, 440, 484, 484.1, 484.2, 461, 467, 469, 471

[56] References Cited

U.S. PATENT DOCUMENTS

| | | | |
|---|---|---|---|
| 3,403,776 | 10/1968 | Denny | 206/56 |
| 3,754,700 | 8/1973 | Bonk | 229/62 |
| 4,352,429 | 10/1982 | Newman | 206/439 |
| 4,660,721 | 4/1987 | Mykleby | 206/439 |
| 4,671,393 | 6/1987 | Rainey | 383/111 |
| 5,062,569 | 11/1991 | Hekal | 206/467 |
| 5,172,812 | 12/1992 | Wharton et al. | 206/469 X |
| 5,222,600 | 6/1993 | Stoddard | 206/370 |
| 5,341,922 | 8/1994 | Cerwin | 206/484.2 |
| 5,459,978 | 10/1995 | Weiss | 53/425 |
| 5,551,781 | 9/1996 | Wilkes | 206/439 |
| 5,590,777 | 1/1997 | Weiss | 206/439 |
| 5,653,090 | 8/1997 | Weiss | 53/425 |
| 5,947,288 | 9/1999 | Dykstra et al. | 206/439 |

*Primary Examiner*—Jacob K. Ackun
*Attorney, Agent, or Firm*—Price, Heneveld, Cooper, DeWitt & Litton

[57] ABSTRACT

A sterilizable package for medical objects or the like, comprising, a first layer of material, a second layer of film on said first layer, a third layer having a preformed blister formed from film on said second layer, the layers being sealed together in a peripheral seal to form a space between the second and third layers for an object, the seal between the first layer and the second and third layers being releasable by tensile separation of the first layer from the second and third layers, and the second layer having a breakable perforation line at the space whereby the second layer can be broken at the perforation line to expose a portion of the object for direct presentation of the object from one person to another person.

19 Claims, 3 Drawing Sheets

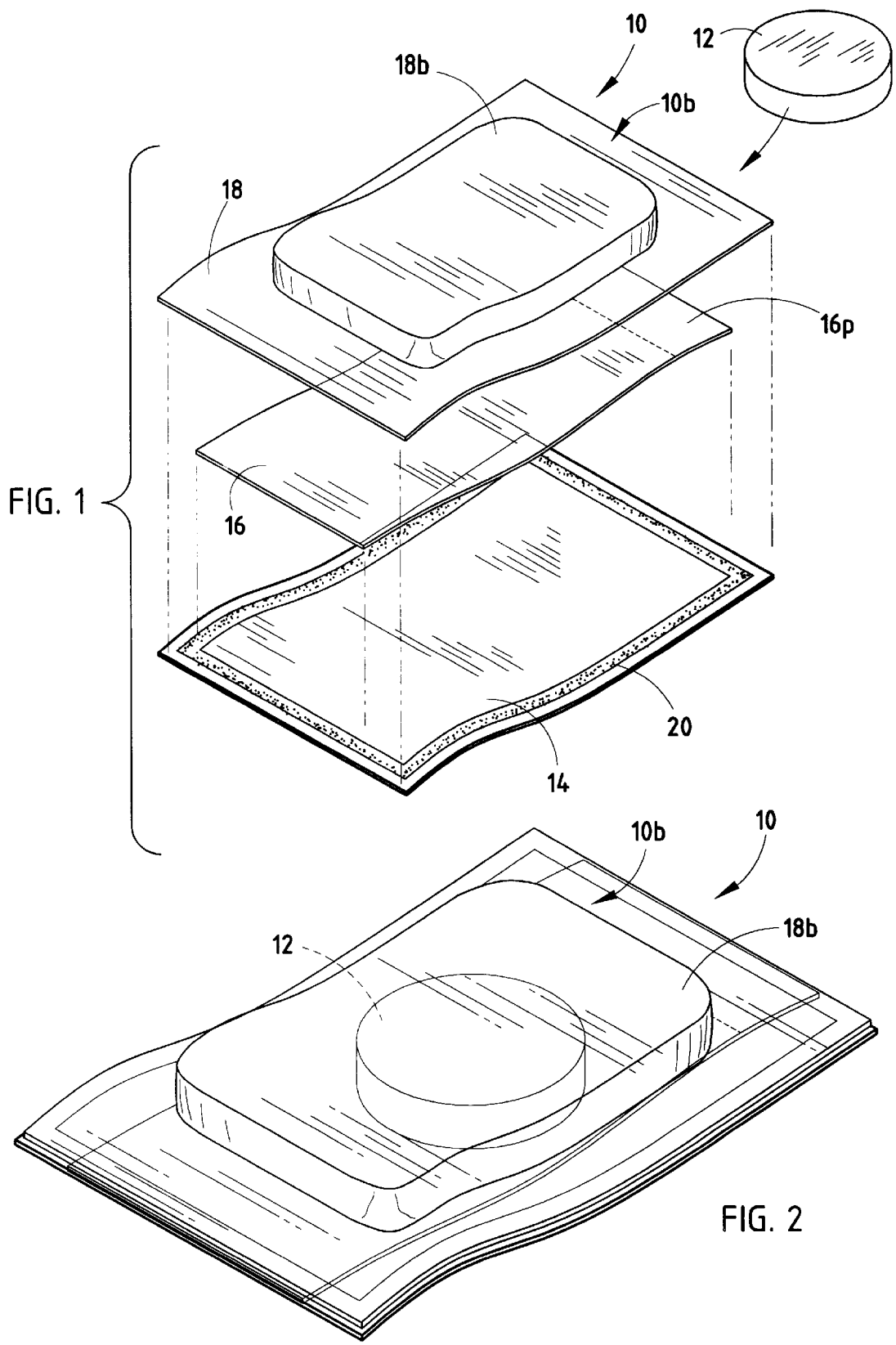

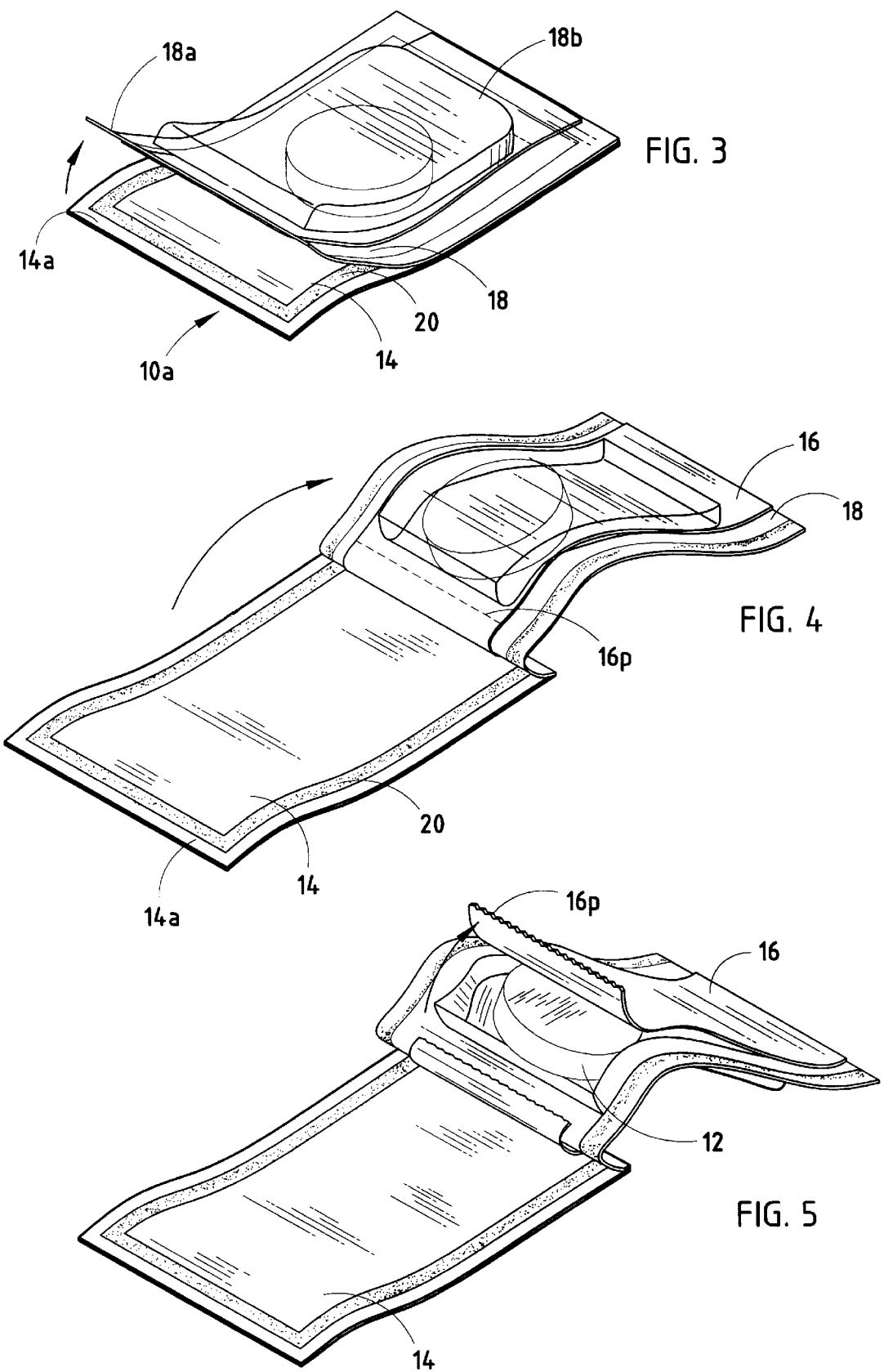

PEEL PACKAGE

RELATED APPLICATION

This application is a continuation-in-part of application Ser. No. 09/179,811, filed Oct. 27, 1998, and entitled PEEL POUCH, now U.S. Pat. No. 5,947,288, incorporated herein by reference.

BACKGROUND OF THE INVENTION

This invention relates to a sterilizable package and a method of making the same. Sterile objects for medical use are retained in packaging intended to allow the sterile object to be uncontaminated when presented to a doctor or surgeon for his/her use. There are presently two primary techniques for retaining sterility. In the first technique, a portion of the peripheral seal of the sterile package (FIG. 8 of U.S. application Ser. No. 09/179,811) is broken between the two layers of the package, and the sterile object is then slid out of the package without touching it, onto a sterile surface such as a table (FIG. 9 of U.S. application Ser. No. 09/179,811), from which the doctor/surgeon removes the object for use in the medical procedure or surgery. Having to use this intermediate sterile surface is a significant disadvantage. A second technique which takes special training to achieve by the medical assistant is accomplished by pulling the sterile package layers apart at one end, peeling or folding back the two layers in opposite directions (FIG. 10 of U.S. application Ser. No. 09/179,811) while the assistant is grasping a portion of the object through the two layers, and allowing the doctor/surgeon to take the object directly from the package as it is presented to him by the nurse or assistant. This technique can result in dropping of the object or other inadvertent contamination of the sterile object.

SUMMARY OF THE INVENTION

The present invention enables an object such as a sterile medical object to be sterilized in the packaging, the package retaining the sterility of the object, but later enabling easy presentation and removal of the object from the package without having to use either of the prior techniques mentioned above. Rather, the object can be presented directly to the surgeon without contact by the presenter, e.g., a nurse, and with minimal possibility of mishap to cause inadvertent contamination of the sterile object.

The package constitutes a unique three layer assembly with the layers being any of several different materials such as polymer, paper, or composite materials such as a paper-polymer combination. The base or first layer may thus be of a selected material and preferably is of a nonwoven, breathable, spun polymeric material, as of a polyolefm, e.g., a material marketed as Tyvek®, by E.I. Du Pont Company. The second, i.e., middle layer, is of selected material and preferably constitutes a polymer film, most preferably transparent, as of polyethylene. The third, i.e., top layer, is of selected material, preferably formed as a three-dimensional blister from a polymer film, most preferably transparent, such as an ethylene-vinyl acetate/Surlyn®/ethylene-vinyl acetate. The sterile object is retained between layers two and three. The second, middle layer, has a transverse perforation line thereacross, which allows it to be broken open at the appropriate time. The sterile object can be removed in a protected fashion by breaking the seal between layer one and the joined layers two and three by pulling the sections apart using protruding gripping flanges, finger force then being applied to break the perforation line so layer one, a portion of broken layer two, and the overlapping portion of layer three can be folded back to expose a portion of the sterile object to enable the surgeon's assistant to present the exposed portion of the sterile object directly to the surgeon for his/her grasp.

These and other features, advantages and objects of the present invention will be further understood and appreciated by those skilled in the art by reference to the following specification, claims and appended drawings.

BRIEF DESCRIPTION OF THE DRAWINGS

FIG. 1 is an exploded view of the three layers of the package and a representative sterile object shown simply as a disc for illustrative purposes;

FIG. 2 is a perspective view of the sterilized object in the package;

FIG. 3 is a perspective view depicting the first step in opening the sterile package by grasping flanges and peeling layers two and three away from base layer one;

FIG. 4 is a perspective view showing the further opening of package layers two and three from base layer one;

FIG. 5 is a perspective view depicting the breakage of the perforation line by finger pressure on the underside of the object against the film layer two having the perforation line, for direct access and grasping of the sterile object as by a gloved doctor/surgeon.

DETAILED DESCRIPTION OF PREFERRED EMBODIMENT

Figure 6:
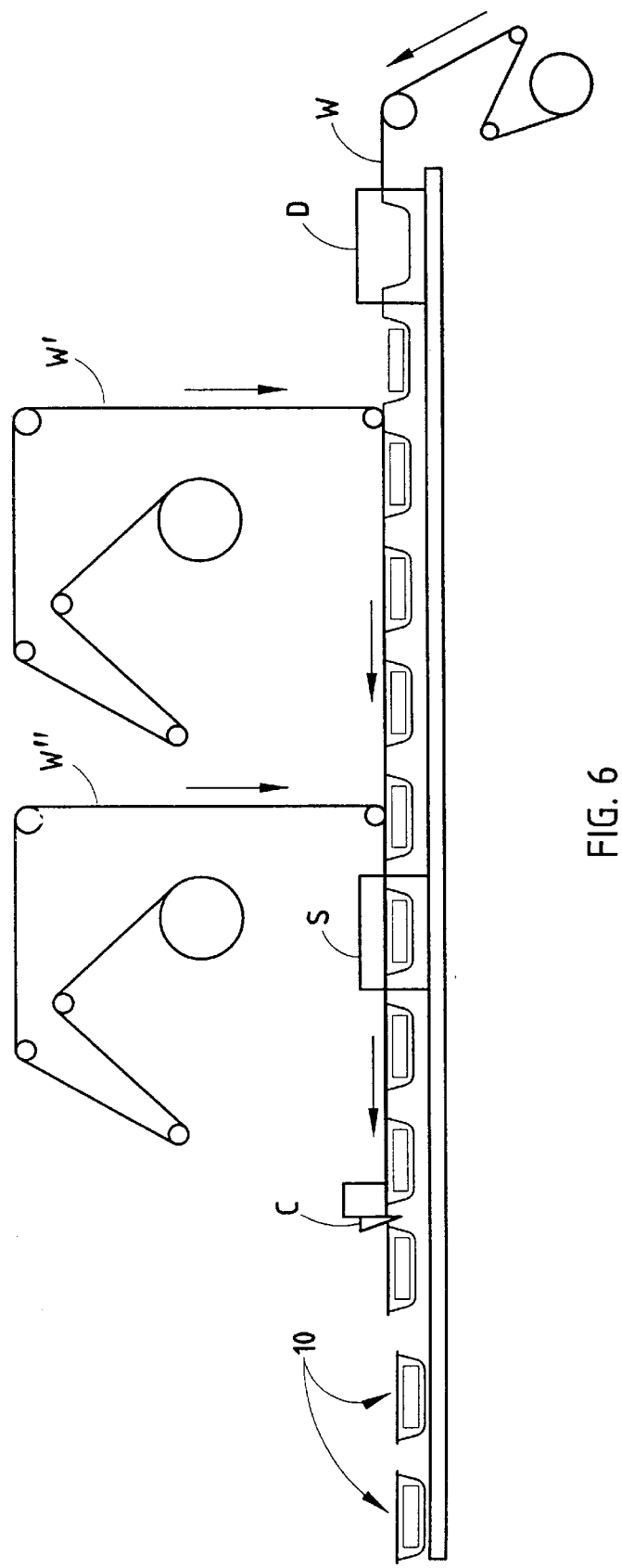
FIG. 6 is an elevational pictorial view depicting formation of the package.

For purposes of clarity, the invention is described in its orientation depicted, it being realized that descriptors such as "up," "down," "top," "bottom," "base," and the like are not limitations, but just used as explanatory terms. Referring now specifically to the drawings, the package assembly 10 is shown to include a representative sterilized object 12 within the sealed assembly. The blister comprises three layers, namely a base layer 14 preferably of a breathable, nonwoven, spun bonded, polyolefin material such as Tyvek® brand; the second layer, i.e., middle layer 16, such as a flexible heat sealable polymer, preferably translucent, and most preferably transparent, as of polyethylene; and the third layer, shown as a top layer 18, having a three-dimensional preformed blister 18b of a heat sealable polymeric layer, preferably translucent and most preferably transparent, as of ethylene-vinyl acetate/Surlyn®/ethylene-vinyl acetate. The first layer 15 may alternatively be of paper, or polymeric film, or paper/film composite, or foil or foil composite. Middle layer 16 is of like length to layers 14 and 18, but narrower from side to side so as to not be sealed along the side edges 16' when the side edges 18' of third layer 18 are sealed to the first layer side edges 14' as will be described. Middle layer 16 has a transverse perforation line 16p that extends thereacross between its side edges, and within the space defined by the side seals. The layers are joined together, preferably by a heat seal, optionally utilizing a hot melt adhesive 20 such as EVA which may be applied over all the surface. The spacing of the seals, i.e., of adhesive 20, from the end edge of layer 14 allows layer 14 to have an extending gripping flange 14a (FIG. 3) i.e. extending beyond the adjacent end seal, and the combined second and third layers to have an extending gripping flange 18a extending beyond the adjacent end seal, for gripping and pulling them apart by the fingers of both hands as generally depicted by the arrow in FIG. 3. Use of a heat sealing adhesive 20 assures excellent sealing between a porous layer 14 and imperforate films 16 and 18. At the side edges of the package, the edges of layer 18 are sealed directly to the edges of layer 14. The side edges of the middle layer 16 are preferably unsealed. At the juncture of the side edges of middle layer 16 with the seal, as depicted at locations 20a in FIG. 1, the seal should assure sufficient adhesive to serve as caulking of the side edges of middle layer 16 for a barrier to contamination.

FIG. 6 depicts one method of forming the novel package, the steps occurring from right to left in the figure. Specifically, a continuous web or film W feeds to a forming die D which repeatedly thermoforms spaced three-dimensional blisters in web W to form pockets. Next the objects 12 are shown placed in the respective pockets or blisters, after which the perforated layer 16 in the form of a continuous film W', transversely perforated at spaced intervals, is applied over the web W and the objects. Next the final layer 14 is applied in the form of a continuous web W". Web W' is sealed to web W between the blisters while web W" is sealed to web W around the periphery of the blisters. This sealing is preferably by a heat sealer S, using a heat responsive adhesive. Finally the individual packages 10 are severed from the strip thereof by a cutting element C.

Manufacture of the package may alternatively include forming continuous web W that will comprise layer 18 of the final package into a series of spaced three-dimensional blisters 18b to form pockets, overlaying this web or layer with a continuous web W' that will form layer 16 of the package, overlaying web W" that will form layer 18 of the package, effecting the seal along the two side edges of webs W and W" and just one end 10a (FIG. 2) of the three layers, but leaving end 10b unsealed. The objects 12 are then inserted between the second and third layers 16 and 18 through this unsealed end 10b from the direction indicated in FIG. 1. End 10b is sealed to bond all three layers together. The product and package are then sterilized in a conventional manner such as by steam, ETO (ethylene oxide) or gamma radiation.

When the sterile object 12 is to be employed in a medical procedure or surgery, the assistant or nurse grasps flange 14a of layer 14 and joined double flange 18a of layers 16 and 18 at end 10a of the package, and peels them apart as shown in FIGS. 3 and 4. At this time, object 12 is still between layers 16 and 18. Then, by applying finger pressure to one side of the object (the underside as depicted in FIGS. 4 and 5) and thumb pressure to the other side of the object, layer 16 is broken across perforation line 16p that extends transversely across the entire width of layer 16 near end 10b of the package, i.e., generally on the opposite end of the inner layers from flanges 14a and 18a. Breakage of this perforation line 16p while grasping with the thumb and fingers the opposite sides of one portion of object 12 enables this portion of the object to be sanitarily held by the assistant while another portion of the object is exposed and presented directly to the surgeon for his grasp of this exposed portion.

Experimental usage of the novel package has shown it to function very effectively.

The above description is considered that of the preferred embodiment only. Modifications of the invention will occur to those skilled in the art and to those who make or use the invention. For example, the generally rectangular configuration of the depicted pouch can be any of a variety of shapes. Therefore, it is understood that the embodiment shown in the drawings and described above is merely for illustrative purposes and not intended to limit the scope of the invention, which is defined by the following claims as interpreted according to the principles of patent law, including the doctrine of equivalents.

What is claimed is:

1. A sterilizable package for medical objects or the like, comprising:
    a first layer of material;
    a second layer on said first layer;
    a third layer on said second layer and comprising a preformed, three-dimensional blister for a sterile object;
    a seal between said first layer and said second and third layers, releasable by tensile separation of said first layer from said second and third layers;
    said second layer having a breakable perforation line at said blister whereby said second layer can be broken at said perforation line to expose a portion of the object in said blister for direct presentation of the object from one person to another person.

2. The sterilizable package in claim 1 wherein said first layer and said second and third layers have graspable flanges extending outwardly beyond said seal, to enable separation of said first layer from said second and third layers, followed by breakage of said perforation line.

3. The sterilizable package in claim 2 wherein said perforation line is located generally on the opposite end of said blister from said flanges.

4. The sterilizable package in claim 1 wherein said seal is a heat seal.

5. The sterilizable package in claim 4 wherein said seal employs a heat seal adhesive.

6. The sterilizable package in claim 1 wherein said first, second and third layers have opposite side edges, and said second layer side edges terminate short of said first and third layer side edges and short of said seal at said side edges.

7. The sterilizable package in claim 1 wherein said first layer is of nonwoven, spun, bonded, olefin material, or paper, or polymeric film, or paper/film composite, or foil or foil composite.

8. The sterilizable package in claim 7 wherein said second and third layers are of polymeric material.

9. The sterilizable package in claim 8 wherein said third layer is translucent.

10. The sterilizable package in claim 8 wherein said third layer is transparent.

11. A sterilizable package for medical objects or the like, comprising:
    a first layer of material;
    a second layer on said first layer;
    a third layer on said second layer in the form of a three-dimensional blister having a peripheral flange;
    said layers being sealed together in a peripheral seal to form an object-receiving space in said blister so as to be between said second and third layers;
    said seal between said first layer and said second and third layers being releasable by tensile separation of said first layer from said second and third layers;
    said second layer having a breakable perforation line at said space whereby said second layer can be broken at said perforation line to expose a portion of the object in said space for direct presentation of the object from one person to another person.

12. The sterilizable package in claim 11 wherein said peripheral seal is incomplete along one peripheral portion of said blister to allow insertion of an object in said space, followed by completing said peripheral seal at said peripheral portion.

13. The sterilizable package in claim 11 wherein said first layer and said second and third layers have graspable flanges extending outwardly beyond said seal, to enable separation of said first layer from said second and third layers, followed by breakage of said perforation line.

14. The sterilizable package in claim 13 wherein said perforation line is located generally on the opposite end of said space from said flanges.

15. The sterilizable package in claim 11 wherein said seal is a heat seal.

16. The sterilizable package in claim 15 wherein said seal employs a heat seal adhesive.

17. The sterilizable package in claim 11 wherein said first, second and third layers have opposite side edges, and said second layer side edges terminate short of said first and third layer side edges and short of said seal at said side edges.

18. The sterilizable package in claim 11 wherein said first layer is of nonwoven, spun, bonded, olefin material, or paper, or polymeric film, or paper/film composite.

19. The sterilizable package in claim 11 wherein said three-dimensional blister is transparent.

* * * * *